United States Patent
Cain, Jr.

(10) Patent No.: US 8,215,174 B2
(45) Date of Patent: Jul. 10, 2012

(54) INSPECTION APPARATUS FOR TUBULAR MEMBERS

(76) Inventor: James M. Cain, Jr., Spring, TX (US)

( * ) Notice: Subject to any disclaimer, the term of this patent is extended or adjusted under 35 U.S.C. 154(b) by 410 days.

(21) Appl. No.: 12/456,453

(22) Filed: Jun. 16, 2009

(65) Prior Publication Data

US 2010/0313664 A1 Dec. 16, 2010

(51) Int. Cl.
*G01N 29/275* (2006.01)
*G01N 29/26* (2006.01)
*G01N 29/06* (2006.01)

(52) U.S. Cl. .......................................................... 73/623

(58) Field of Classification Search ............ 73/622–623, 73/633–635, 637–638, 644; 376/249–252
See application file for complete search history.

(56) References Cited

U.S. PATENT DOCUMENTS

| | | | | |
|---|---|---|---|---|
| 3,121,324 A | * | 2/1964 | Cowan | 73/623 |
| 3,169,393 A | * | 2/1965 | Stebbins | 73/611 |
| 4,055,989 A | * | 11/1977 | Henry et al. | 73/588 |
| 4,127,033 A | * | 11/1978 | Warren et al. | 73/622 |
| 4,586,380 A | * | 5/1986 | Patterson | 73/623 |
| 4,686,078 A | * | 8/1987 | Zwart, Jr. | 376/249 |
| 5,189,915 A | * | 3/1993 | Reinhart et al. | 73/623 |

* cited by examiner

*Primary Examiner* — Hezron E Williams
*Assistant Examiner* — Rose M Miller
(74) *Attorney, Agent, or Firm* — Keaty Law Firm, LLC

(57) ABSTRACT

An ultrasonic inspection system useful for inspecting a tubular member provides for the use of ultrasonic transducer assembly for detecting weld flaws or other out-of range conditions in the tubular member. According to the invention, the tubular member is positioned horizontally on a rolling carriage and a predetermined amount of sound-conductive fluid is deposited into the tubular member. Wide rings secured to opposing open ends of the tubular member prevent the liquid from escaping, while forming a barrier for retaining a given level of liquid inside the tubular member. The transducers are submerged in the liquid and transmit/ receive sonic booms from reflected medium inside the tubular member. The transducers are connected to a computing control unit, which receives signals generated by the transducers and creates a report of any out-of range condition.

18 Claims, 2 Drawing Sheets

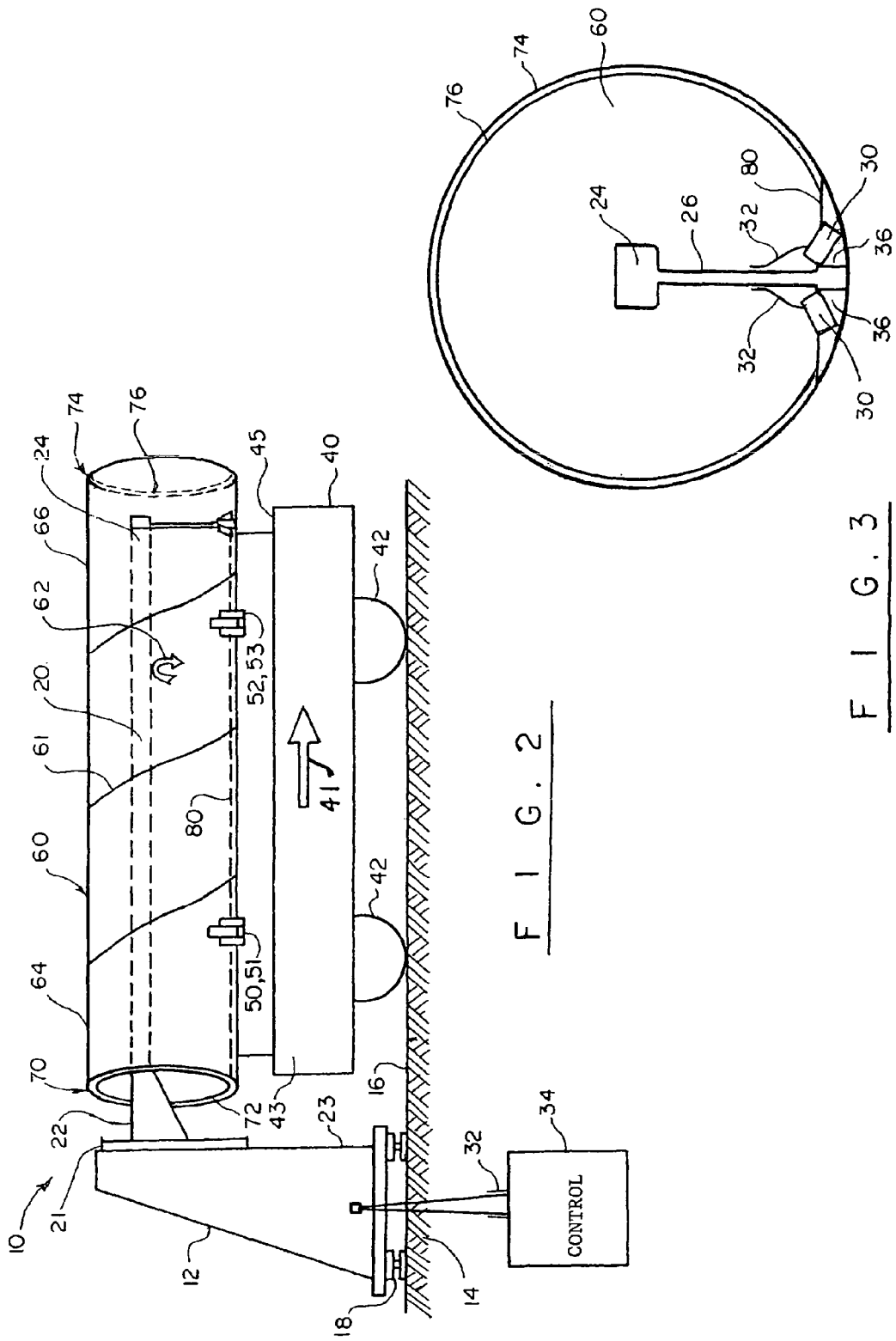

ary of the invention.

INSPECTION APPARATUS FOR TUBULAR MEMBERS

BACKGROUND OF THE INVENTION

The present invention relates to an inspection apparatus, and more particularly, to an inspection apparatus suitable for inspecting tubular members, such as pipes.

Pipelines of various lengths and sizes are widely used in a variety of industries, transporting oil, gas, particulate matter, small solids suspended in fluids and other materials. Pipelines are installed underground and underwater, which results in the pipelines being subject to often harsh environmental conditions including temperature variations, deep sea pressures, and the like. With time, the environment causes pipelines to weaken, sometimes crack along the weld seams, often times corrode. Should the pipeline integrity become compromised, the material traveling along the pipeline may escape and cause substantial damage to the environment.

As a consequence, considerable efforts are dedicated to the inspection of the pipes during manufacturing process. Visual inspection may serve its purpose when the defects are visible. However, visible inspection has its limitations particularly inspection of the inner surface weld may become inefficient and expensive.

The industry has developed a variety of tools to facilitate detection of weld defects in tubular members. Some inspection devices use magnetic force created by magnetizing coils for inducing a magnetic field in the ferrous pipe. Inspection sensor measures changes in the induced magnetic field and produce signals representative of those changes. An analog-to-digital converter digitizes the measured signals representing the changes in the induced magnetic field. Other devices employ ultrasonic inspection methods that use sonic beams to locate defects in tubular members. Some ultrasonic devices use transducers that transmit sonic beams and receive reflected beams from inner and outer surfaces of the pipe, and from defects of the tubular members. In general, this technology is based on the speed of sound in metal and the fact that a sound wave will reflect ("echo") from medium interfaces Conventional techniques involve spraying of water on the outside of the pipe and then applying the sonic boom to uncover potential defects in the weld. However, this method relies largely on the experience of the technician performing the test. Human error can affect the results of the test, leading to missed imperfections in the weld. Therefore, a need exists for an inspection apparatus capable of providing information of defects in a pipe and capable of being easily operated during an inspection.

The present invention contemplates elimination of drawbacks associated with conventional technique and provision of an improved system and method of tubular members testing and inspection that is easy to use and operate.

SUMMARY OF THE INVENTION

It is, therefore, an object of this invention to provide an apparatus of for inspecting tubular members.

It is another object of the invention to provide a system and method for inspecting tubular members using ultrasound technology.

It is a further object of the invention to provide a system and method of inspecting welds made in the tubular members using ultrasound technology.

These and other objects of the invention are achieved through a provision of an ultrasonic inspection system useful for inspecting a tubular member provides for the use of ultrasonic transducer assembly for detecting weld flaws or other out-of range conditions in the tubular member. According to the invention, the tubular member is positioned horizontally on a rolling carriage and a predetermined amount of sound-conductive fluid is deposited into the tubular member. Wide rings secured to opposing open ends of the tubular member prevent the liquid from escaping, while forming a barrier for retaining a given level of liquid inside the tubular member. The transducers are submerged in the liquid and transmit/receive ultrasonic signals from reflected medium inside the tubular member. The transducers are connected to a computing control unit, which receives signals generated by the transducers and creates a report of any out-of range condition.

BRIEF DESCRIPTION OF THE DRAWINGS

Reference will now be made to the drawings, wherein like parts are designated by like numerals, and wherein

FIG. 2 is a perspective side view of the apparatus of the present invention.

FIG. 3 is an end view of the tubular member being tested, showing position of ultrasonic transducers.

DETAILED DESCRIPTION OF THE INVENTION

Figure 1:
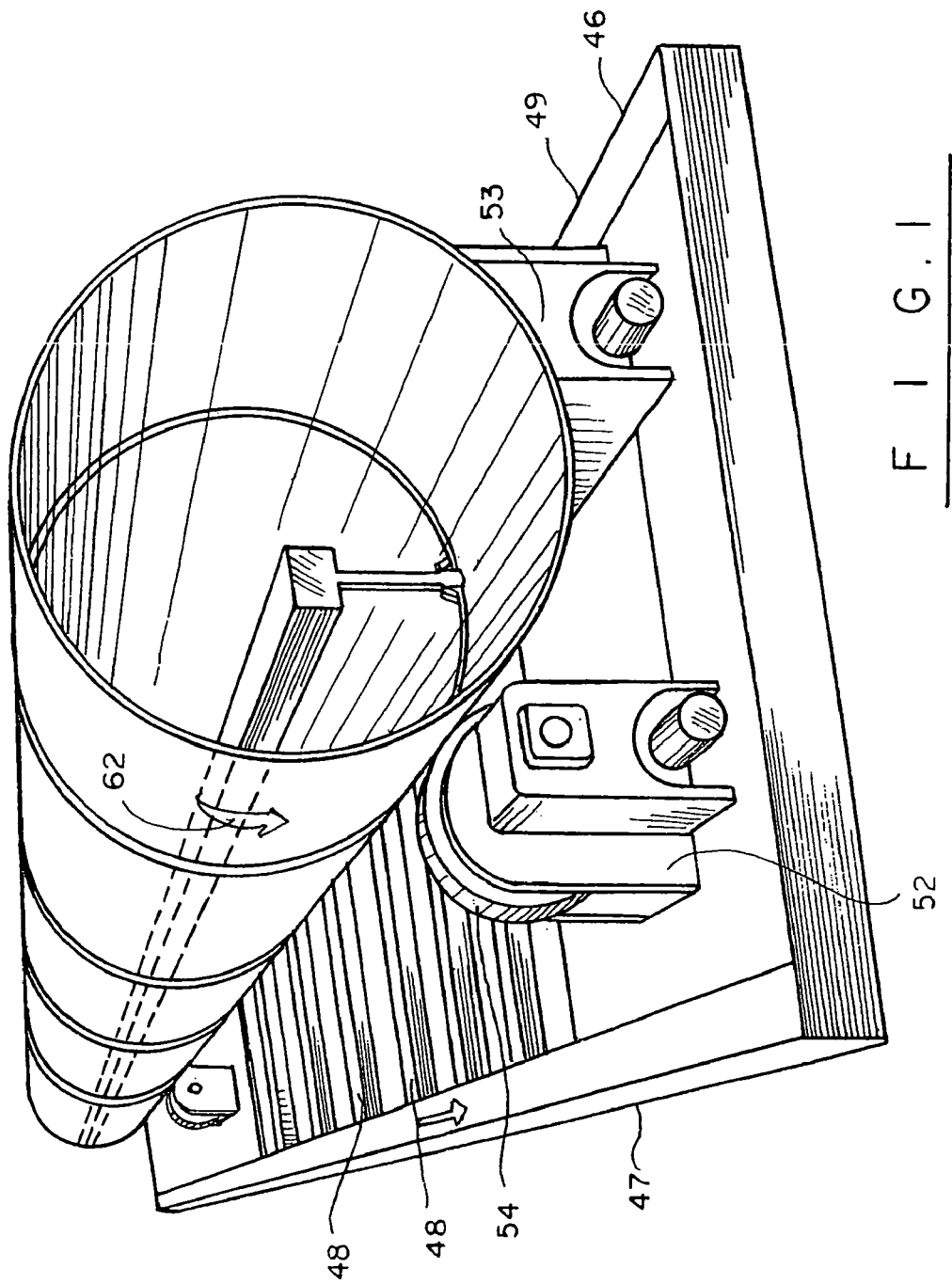
FIG. 1 is a perspective end view of a tubular member mounted on a carriage of the apparatus of the present invention.

Turning now to the drawings in more detail, numeral 10 designates the pipe testing apparatus of the present invention. The apparatus 10 comprises an upright pedestal 12 positioned on the ground 14 at or near railway tracks 16. The pedestal 12 can be elevated using the legs 18 for alignment with a tubular member being tested and positioned on a carriage. An elongated beam 20 is secured at a proximate end 22 thereof to the pedestal 12. The beam 20 is cantilevered from the pedestal 12 and extends transversely to an attachment plate 21 secured to a front surface 23 of the pedestal 12. The length of the beam 20 is selected to approximate the length of a tubular member 30 being inspected. A supporting bracket 26 is secured to a distant end 24 of the beam 20. The bracket 26 extends downwardly from the beam 20, supporting the array of ultrasonic transducers 30 by a free end thereof.

A carriage assembly 40 for laterally supporting a tubular member is mounted on rotating wheels 42. The carriage assembly 40 is configured for movement along the tracks 16 in the direction of arrow 41 and back while being supported by the wheels 42. Alternatively, the wheels 42 may be adapted for movement on the ground. The carriage assembly 40 comprises a generally rectangular frame 46 having a plurality of reinforcing beams 48 extending between a first side 47 and a second side 49 of the frame 46.

A first set of rollers 50, 51 is secured on the frame 46 adjacent a proximate end 43 of the carriage assembly 40. A second set of rollers 52, 53 is positioned adjacent a distant end 45 of the carriage assembly 40. The first set of rollers 50, 51 are spaced from each other and are oriented in a generally parallel position. The second set of rollers 52, 53 is similarly spaced from each other and oriented in parallel relationship. The rollers 50, 52 are aligned along the same plane and are positioned adjacent the side 47 of the frame 46. The rollers 51, 53 are similarly aligned along the same plane and are positioned adjacent the side 49 of the frame 46.

The rollers 50, 51, 52, and 53 each have rotating members 54 (only one rotating member 54 is shown in FIG. 1) that are configured for supporting a tubular member 30, while allowing the tubular member 30 to be rotated about its axis in the direction of arrow 62 during testing. The rollers 50, 51, 52, and 53 may be connected to an external power source for imparting rotation on the rotating members 54, if desired.

Each ultrasonic transducer 30 is provided with cables 32, which operationally connect the transducers 30 to a sound generating, processing and control unit 34. The control unit 34 may be mounted on the pedestal 12, if desired. As can be seen in FIG. 3, each of the transducers 30 comprises a generally rectangular housing that is adapted to be positioned inside the tubular member 60 in close proximity to the wall of the tubular member 60. An optional block 36 may be provided for orienting respective transducer housing inside the pipe 60. The blocks 36 may be formed as wedges adapted for resting on the inside wall of the pipe 60.

A ring-shaped member 70 is positioned on a proximate open end 64 of the tubular member 60. The inner circumferential edge 72 of the ring 70 extends inwardly toward the center of the pipe 60. A similar ring-shaped member 74 is positioned on a distant open end 66 of the pipe 60. An inner circumferential edge 76 of the ring 74 extends a distance toward the center of the pipe 60. The rings 70, 74 may be formed of rubber or other non-corrosive material. The rings 70, 74 may have a width of about 2-3", or other width sufficient to flood a portion of the pipe interior and submerge the transducers 30.

The rings 70 and 74 form a watertight circumferential wall, or barrier that allows water or other sound-conductive liquid to be retained in the pipe 60 during testing. As can be seen in FIGS. 2 and 3, the water level 80 does not extend beyond the inner edges 72, 76 of the rings 70, 74. At the same time, the transducers 30 become partially or entirely submerged when positioned inside the tubular member 60.

In operation, the apparatus 10 is delivered to a testing site, where the pipes 60 are welded. The weld seams 61, usually made on a spiral along the length of the pipe 60 are inspected using the system of the present invention. The tubular member 60 is positioned on the carriage assembly 40, on top of the rolling members 54. The rings 70 and 74 are secured on the ends 64, 66 of the pipe 60, respectively. Water is then deposited into the cavity defined by the inside wall of the pipe 60 and the inner edges 72, 76 of the rings 70, 74.

The carriage is then moved toward the pedestal 12, allowing the beam 20 to extend inside the tubular member 60 and to suspend the transducers 30 in a submerged position, below the water level 80, inside the tubular member 60. The cables 32 are connected between the transducers 30 and the computing control unit 34. Rotation is then imparted on the pipe 60, allowing the water to be moved by gravity inside the pipe 60. At the same time, the control unit 34 energizes the transducers 30 to send and receive sound waves.

In general, the instant method is based on the speed of sound in metal and water, as well as the fact that a sound wave will reflect ("echo") from medium interfaces. Thus by propagating a sonic wave in the water and by measuring the time it takes for echo of that wave to return from an interface, it is possible to determine the precise distance to the interface. Such interface may be the weld 61 on the wall of the tubular member 60. In order to determine the wall thickness (or insufficient weld thickness) in the tubular member 60 about the whole area of the tubular member 60, the tubular member is rotated about its axis and advanced longitudinally in relation to the transducers 30, which periodically "fire" and effectively sample the weld thickness under the transducers 30 at the time. As the pipe 30 advances a stream of data points, each one representing a weld quality, measurement is generated.

The data resulting from testing is displayed on a screen of the control unit 34. Out-of-range values can be detected either by human reading or by a computer detection of out of range values. From such data the general location of a suspected defect along the length of the weld in the tubular member, its magnitude and direction (whether too thin or too thick) can be determined. The operator can then identify the pipe as acceptable for use or as requiring repairs.

To facilitate generation of readable data, the blocks 36 can be inclined so that the transducers 30 are held in a position relative to the pipe surface to transmit a short duration sonic wave pulse of beamed energy into the wall of the pipe at an angle such that a flaw or discontinuity in the weld 61 causes the waves to be reflected back and produce a signal indicative of an out-of-range condition.

In one of the preferred embodiments, the transducers are oriented to send sonic waves in opposite directions, so that a given defect that may be invisible to one transducer 30 looking at it from one direction becomes visible to a second transducer 30 looking at it from the opposite direction. Once the inspection of the pipe 60 is completed, the tubular member 60 is removed from the carriage 40, and another tubular member is positioned on the carriage 40 for inspection. The report generated by the control unit 34 is analyzed. If a defect is found, the tubular member 60 is repaired; if no defects are detected, the pipe 60 may be accepted for field use.

The apparatus of the present invention allows inspection of an entire length of the tubular member 60, end-to-end. Depending on the particular application, the length of the beam 20 can be modified in order to cover the length of the pipe 60 being inspected. Combined with the ability of the carriage 40 to travel longitudinally, the apparatus of the instant invention allows defection of out-of-range conditions along the walls of the tubular member regardless of the size of the pipe.

Many changes and modifications can be made in the design of the present invention without departing from the spirit thereof. I therefore pray that my rights to the present invention be limited only by the scope of the appended claims.

I claim:

1. An ultrasonic inspection device useful for inspecting a tubular member comprising:
   a carriage assembly configured for laterally supporting the tubular member in a generally horizontal position and laterally moving the tubular member during testing, said carriage assembly comprising rollers allowing axial rotation of the tubular member;
   an elongated beam extendable through an interior of the tubular member, said elongated beam carrying transducers for transmitting sonic beams and for receiving reflected beams thereof from an inner surface of the tubular member and from defects of the tubular member;
   a means for retaining a predetermined amount of sound-conductive liquid in the interior of the tubular member without sealing the interior of the tubular member; and
   a control unit operationally connected to the transducers, said control unit analyzing signals generated by the transducers and creating a report indicate of an out-of range condition in the tubular member.

2. The apparatus of claim 1, wherein said means for retaining the sound-conductive liquid comprises a pair of ring-shaped members configured for circumferentially engaging a respective open end of the tubular member, each of said ring-shaped members having an inner edge extending toward a center of the tubular member.

3. The apparatus of claim 2, wherein each of said ring-shaped members has a width sufficient for forming a watertight barrier preventing escape of the sound-conductive liquid from interior of the pipe.

4. The apparatus of claim 2, wherein said ring-shaped members have a pre-selected width for retaining a level of sound-conductive liquid in the interior of the tubular member sufficient for at least partially submerging the transducers.

5. The apparatus of claim 1, further comprising an upright pedestal supporting said elongated beam inside the tubular member.

6. The apparatus of claim 1, further comprising an upright pedestal, from which the elongated beam extends as a cantilevered member.

7. The apparatus of claim 1, wherein said carriage assembly further comprises rotating wheels for rotatably supporting the carriage assembly on tracks or on the ground.

8. The apparatus of claim 1, further comprising a bracket attached to a distant end of the elongated beam, said bracket extending downwardly from the beam transversely to a longitudinal axis of the tubular member and securing the transducers in a position below the surface of the sound-conductive liquid deposited in the tubular member.

9. The apparatus of claim 1, further comprising a means for angularly orienting the transducers configured for resting on an inside wall of the tubular member.

10. The apparatus of claim 9, wherein said means for angularly positioning the transducers comprises a wedge-shaped member configured for supporting a respective transducer below the level of liquid deposited into the interior of the pipe.

11. An ultrasonic inspection device useful for inspecting a tubular member comprising:
   an upright pedestal;
   an elongated beam secured at one of its ends to the upright pedestal and extending in a cantilevered position from the upright pedestal, said elongated beam configured for extending into the interior of the tubular member;
   a carriage assembly configured for laterally supporting the tubular member in a generally horizontal position and laterally moving the tubular member during testing, said carriage assembly comprising rollers allowing axial rotation of the tubular member positioned on the carriage assembly;
   a transducer assembly for transmitting sonic beams and for receiving reflected beams thereof from an inner surface of the tubular member and from defects of the tubular member, said transducer assembly being suspended from a free end of the elongated beam;
   a means for retaining a predetermined level of sound-conductive liquid in the interior of the tubular member without sealing the interior of the tubular member, said liquid level being sufficient to submerge the suspended transducer assembly; and
   a control unit operationally connected to the transducers, said control unit analyzing signals generated by the transducers and creating a report indicate of an out-of range condition in the tubular member.

12. The apparatus of claim 11, wherein said means for retaining the sound-conductive liquid comprises a pair of ring-shaped members configured for circumferentially engaging a respective open end of the tubular member, each of said ring-shaped members having an inner edge extending toward a center of the tubular member, said ring shaped members forming a barrier for retaining the liquid level inside the tubular member.

13. The apparatus of claim 11, wherein said carriage assembly further comprises rotating wheels for rotatably supporting the carriage assembly on tracks or on the ground.

14. The apparatus of claim 11, further comprising a bracket attached to the free end of the elongated beam, said bracket extending downwardly from the beam transversely to a longitudinal axis of the tubular member and securing the transducers in a position below the surface of the sound-conductive liquid deposited in the tubular member.

15. A method of inspecting a tubular member, comprising the steps:
   orienting the tubular member in a substantially horizontal position;
   positioning the tubular member in a position to receive rotating force;
   depositing and retaining a sound-conductive liquid in an interior of the tubular member without sealing the interior of the tubular member;
   suspending transducers inside the tubular member below the liquid level of the sound-conductive liquid;
   imparting rotation on the tubular member about a horizontal axis;
   transmitting sonic beams and receiving reflected beams thereof from an inner surface of the tubular member and from defects of the tubular member; and
   generating signals indicative of an out-of range conditions in the tubular members.

16. The method of claim 15, further comprising a step of processing the generated signals using a computing device.

17. The method of claim 15, further comprising a step of rotating the tubular member about its axis while transmitting and receiving the sonic beams.

18. The method of claim 15, further comprising a step of laterally moving said tubular member while retaining the transducers in a stationary position so as to inspect the entire length of the tubular member.

* * * * *